United States Patent
Kirsch et al.

(10) Patent No.: US 10,181,316 B2
(45) Date of Patent: Jan. 15, 2019

(54) DYNAMICALLY INCREASED NOISE SUPPRESSION BASED ON INPUT NOISE CHARACTERISTICS

(71) Applicant: Continental Automotive Systems, Inc., Auburn Hills, MI (US)

(72) Inventors: Matthew R. Kirsch, Amsterdam (NL); Guillaume Lamy, Chicago, IL (US); Bijal Joshi, Elk Grove Village, IL (US)

(73) Assignee: Continental Automotive Systems, Inc., Auburn Hills, MI (US)

( * ) Notice: Subject to any disclaimer, the term of this patent is extended or adjusted under 35 U.S.C. 154(b) by 0 days.

(21) Appl. No.: 15/584,786

(22) Filed: May 2, 2017

(65) Prior Publication Data

US 2018/0075836 A1  Mar. 15, 2018

Related U.S. Application Data

(60) Provisional application No. 62/393,075, filed on Sep. 11, 2016.

(51) Int. Cl.
*G10K 11/34* (2006.01)
*A61B 6/00* (2006.01)
(Continued)

(52) U.S. Cl.
CPC .......... *G10K 11/343* (2013.01); *A61B 6/5264* (2013.01); *G10K 11/04* (2013.01);
(Continued)

(58) Field of Classification Search
CPC .... G10K 11/343; G10K 11/04; G10K 11/178; G10K 11/1782; G10K 2210/108; G10K 2210/1081; G10K 2210/12821; G10K 2210/3016; G10K 2210/3051; G10K 2210/3056; A61B 6/5264; A61F 2011/145
(Continued)

(56) References Cited

U.S. PATENT DOCUMENTS 4,811,404 A * 3/1989 Vilmur ................ G10L 21/0208
327/552
2005/0240401 A1* 10/2005 Ebenezer ............ G10L 21/0208
704/226

FOREIGN PATENT DOCUMENTS

| EP | 2466581 A2 | 6/2012 |
|---|---|---|
| WO | 99/62054 A1 | 12/1999 |
| WO | 2005/109404 A2 | 11/2005 |

OTHER PUBLICATIONS

Search Report dated Mar. 23, 2017, from corresponding GB Patent Application No. GB1617278.5.

* cited by examiner

*Primary Examiner* — Jason R Kurr

(57) ABSTRACT

A maximum noise suppression level ($G_{min}$) is not a single constant value for an entire frequency range, but is allowed to vary across frequencies. The amount of variation is dynamically computed based on the input noise characteristics. For example, if there is excess noise in the lower frequency region, the maximum noise suppression level in that region will increase to suppress the noise in that frequency region. This feature can be enabled all the time, and will be active when the input conditions warrant extra noise suppression in a particular frequency region. Thus, the effort involved in manually tuning an audio system (e.g., hands-free telephony, voice-controlled automotive head unit, etc.) can be significantly reduced or eliminated.

20 Claims, 12 Drawing Sheets

(51) Int. Cl.
*G10K 11/04* (2006.01)
*G10K 11/178* (2006.01)
*G10L 21/0208* (2013.01)
*A61F 11/14* (2006.01)

(52) U.S. Cl.
CPC ........ G10K 11/178 (2013.01); G10L 21/0208 (2013.01); *A61F 2011/145* (2013.01); *G10K 2210/108* (2013.01); *G10K 2210/1081* (2013.01); *G10K 2210/12821* (2013.01); *G10K 2210/3016* (2013.01); *G10K 2210/3051* (2013.01); *G10K 2210/3056* (2013.01)

(58) Field of Classification Search
USPC ...................... 381/94.3; 379/406.01, 406.12; 455/569.1, 569.2, 570
See application file for complete search history.

DYNAMICALLY INCREASED NOISE SUPPRESSION BASED ON INPUT NOISE CHARACTERISTICS

BACKGROUND

Hands-free audio systems in automobiles can be used without the use of hands (for example via voice commands) or, in a wider sense, with relatively limited use of hands such that a telephone handset does not need to be held in the driver's hand while the driver is driving an automobile.

Automotive hands-free audio systems commonly use one or more of the vehicle's speakers to transmit the voice of the person on the other end of the telephone call, and one or more microphones in the vehicle to capture the driver's and/or passengers' voices during telephone calls.

A mobile phone is commonly connected to an automotive audio system head unit or a telematics unit in the vehicle via Bluetooth. Or the head unit or telematics unit could have its own network access device (NAD). In such a system, as the microphone signal goes through the system, the signal is processed and sent to the person on the other end through the mobile phone or NAD. The speech from the far end is coming through the phone (through the Bluetooth) or NAD, being processed, and then comes out of the speakers.

At the microphone in the vehicle, there could be near end speech, background noise, wind noise, and echo, which is the audio coming from the audio-system speakers and which is also being picked up by the microphone. When the person on the far end is speaking, that person doesn't want to hear their echo, the road noise, or the wind noise. So, the echo is typically cancelled, the road noise is typically suppressed, which are common features, but noise-suppression techniques that dynamically increase noise suppression based on input noise characteristics would improve the performance of a hands-free audio system, for example, by improving the sound quality at the far end of telephone conversations in which an automotive hands free audio system is being used and/or by improving speech-recognition performance of a voice-controlled application.

BRIEF SUMMARY

In accordance with embodiments of the invention, a maximum noise suppression level ($G_{min}$) is not a single constant value for an entire frequency range, but is allowed to vary across frequencies. The amount of variation is dynamically computed based on the input noise characteristics. For example, if there is excess noise in the lower frequency region, the maximum noise suppression level in that region will increase to suppress the noise in that frequency region. This feature can be enabled all the time, and will be active when the input conditions warrant extra noise suppression in a particular frequency region. Thus, the effort involved in manually tuning an audio system (e.g., hands-free telephony, voice-controlled automotive head unit, etc.) can be significantly reduced or eliminated.

DETAILED DESCRIPTION

Some vehicles have noise that has very high low-frequency content (e.g., when equipped with a diesel engine). One way to cope with such elevated low frequency noise is the use of high-pass filters. However, high-pass filters indistinctly remove both speech and noise, which results in a degradation of the speech quality (speech sounds less full and less natural). Alternatively, the maximum noise suppression level could be increased, but this will affect the entire frequency spectrum and may lead to an overall degradation in speech quality due to higher than necessary noise suppression in the middle and higher frequency regions.

In accordance with embodiments of the invention, the maximum noise suppression level ($G_{min}$) is no longer one constant value for the entire frequency range, but is allowed to vary across frequencies. The amount of variation is dynamically computed based on the input noise characteristics. For example, if there is excess noise in the lower frequency region, the maximum noise suppression level in that region will increase to suppress the noise in that frequency region. This feature can be enabled all the time, and will be active when the input conditions warrant extra noise suppression in a particular frequency region. Thus, the effort involved in manually tuning an audio system (e.g., hands-free telephony, voice-controlled automotive head unit, etc.) can be significantly reduced or eliminated.

Figure 1:
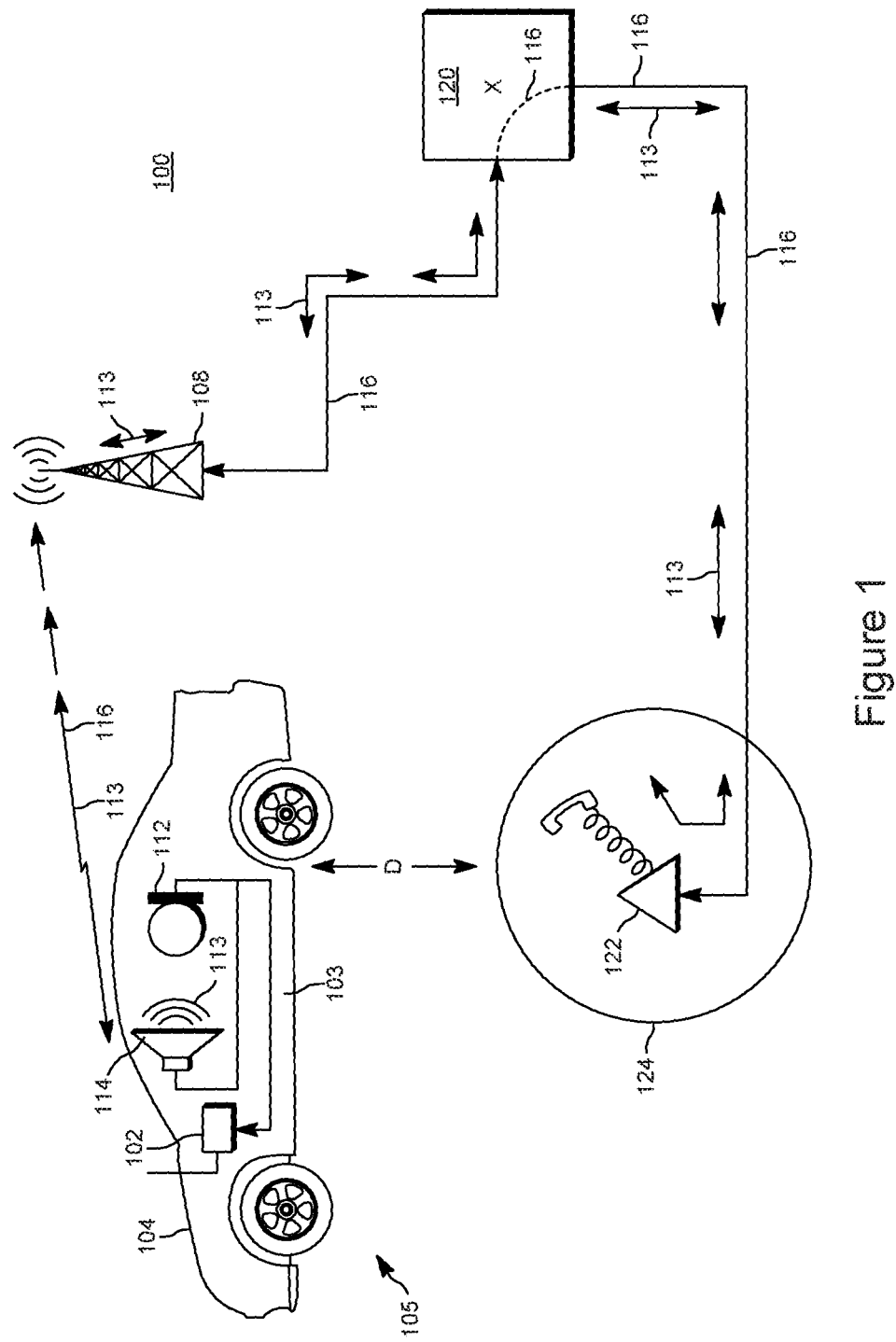
FIG. 1 depicts an example operating environment 100 for embodiments of the invention.

FIG. 1 depicts an example operating environment 100 for embodiments of the invention. The operating environment 100 shown in FIG. 1 comprises a wireless communications device 102, usable by occupants of a passenger compartment or cabin of a vehicle 104. The wireless communications device 102 provides two-way wireless communications that include voice communications, which are facilitated by a wireless network 108 that is compatible with the wireless communications device 102.

In the vehicle 104, the hands-free audio system 105 comprises a microphone 112 or multiple microphones (only one shown) and a loudspeaker 114 or multiple loudspeakers (one shown). The microphone 112 transduces or "picks up" audio-frequency signals from within the passenger compartment or interior 103 of the vehicle 104 and provides electrical signals representing those audio signals to the wireless communications device 102 via a controller 130 for the hands-free audio system 105. The microphone 112 thus picks up road noise, wind noise, and engine noise caused by the vehicle being driven about as well as audio signals output from loudspeakers 114 in the cabin 103, including audio signals that are returned from the far end of a telecommunications path, referred to as "echo."

The loudspeaker 114 portion of the hands-free system 105 receives electrical signals in the audio-frequency range from the wireless communications device 102 via the controller 130 for the hands-free audio system 105. The loudspeaker 114 transduces those electrical signals into sound waves or audio signals 113 that can be heard throughout the passenger compartment 103 of the vehicle 104.

Audio signals 113 picked up by the microphone 112 are converted to electrical signals representing the audio signals. The electrical signals are provided to the wireless communications device 102. The wireless communications device 102 transmits radio frequency signals containing the electrical signals obtained from the microphone to the wireless communications network 108 where they are routed from the network 108 to a conventional telephone switching system 120.

The telephone switching system or network 120 switches or routes the audio signals 113 obtained from the vehicle 104 to a communications device, such as a mobile phone or a conventional telephone handset 122, which is located at a distant location 124, i.e. a location remotely located away from the vehicle 104 at a distance, D. The voice-frequency communications 113 that take place between a person in the vehicle 104 and a person at the distant/remote location 124 thus takes place via a communications link or channel identified in FIG. 1 by reference numeral "116."

The hands-free audio system 105 may also be embodied as a voice-controlled audio system, such as, an automotive head unit or an automotive telematics unit, as a couple of examples.

Figure 2:
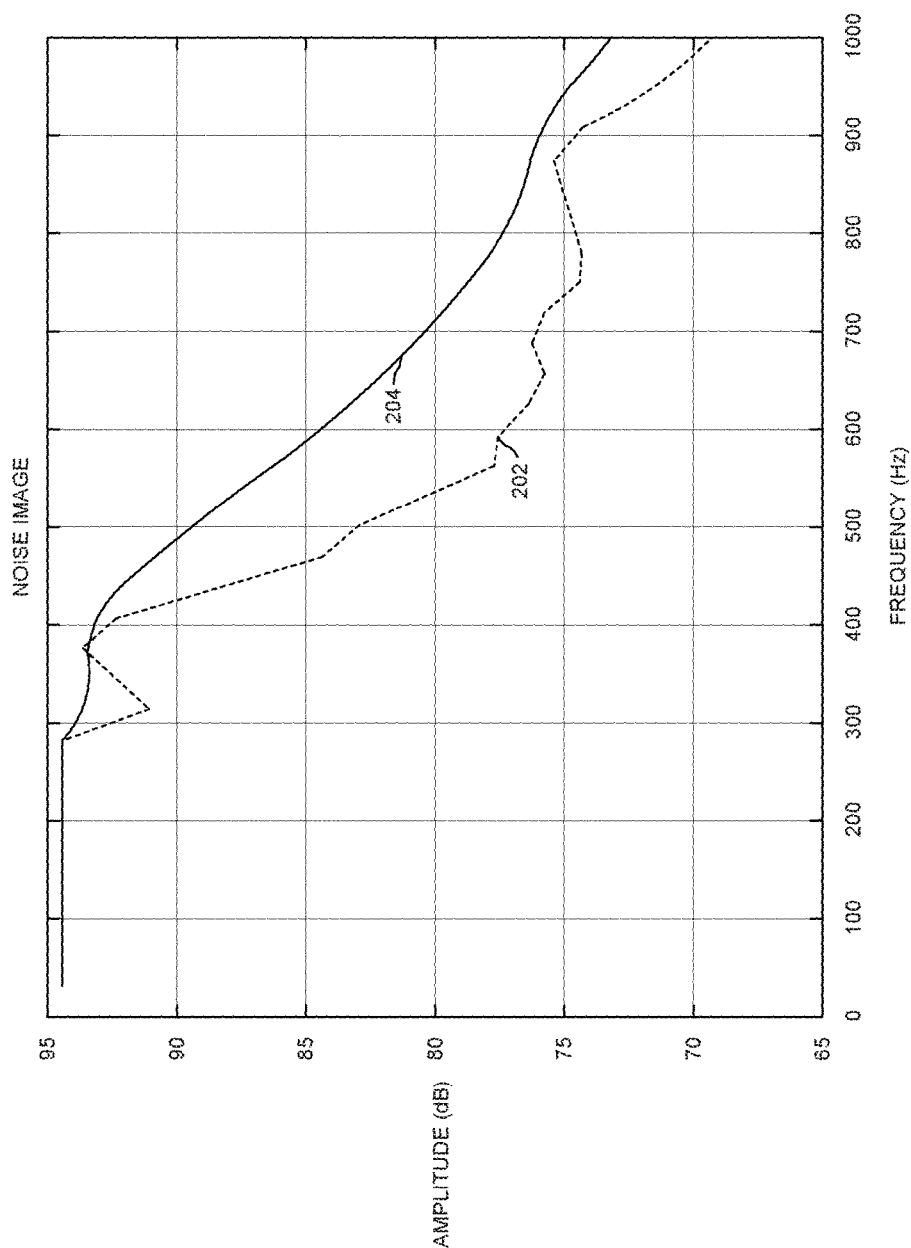
FIG. 2 depicts an example of an original noise image and a corresponding smoothened out (low-pass filtered) original noise image.

In a first embodiment, an original noise image noise_orig is smoothened out (low-pass filtered) over frequency to form noise_smooth:

noise_smooth[0]=noise_orig[0]

noise_smooth[$i$]=$\alpha$*noise_orig[$i$]+(1-$\alpha$)*noise_smooth[$i$-1], $i$=1,2, . . . , $N$-1 where $\alpha$=0.25, i is the frequency channel index, and N is the number of frequency channels that will be considered (this is parameter-controllable; preferred value corresponds to 1000 Hz). FIG. 2 depicts an example of noise_orig 202 and a corresponding smoothened out (low-pass filtered) noise_smooth 204.

The smoothened noise image 204 is then inverted and normalized:

$$\text{noise\_smooth}_{inv}[i] = \frac{1}{\text{noise\_smooth}[i]},$$

$i = 0, 1, \ldots, N-1$ $$\text{noise\_smooth}_{inv,norm}[i] = \frac{\text{noise\_smooth}_{inv}[i]}{\max_{\forall i}(\text{noise\_smooth}_{inv})},$$

$i = 0, 1, \ldots, N-1$

Figure 3:
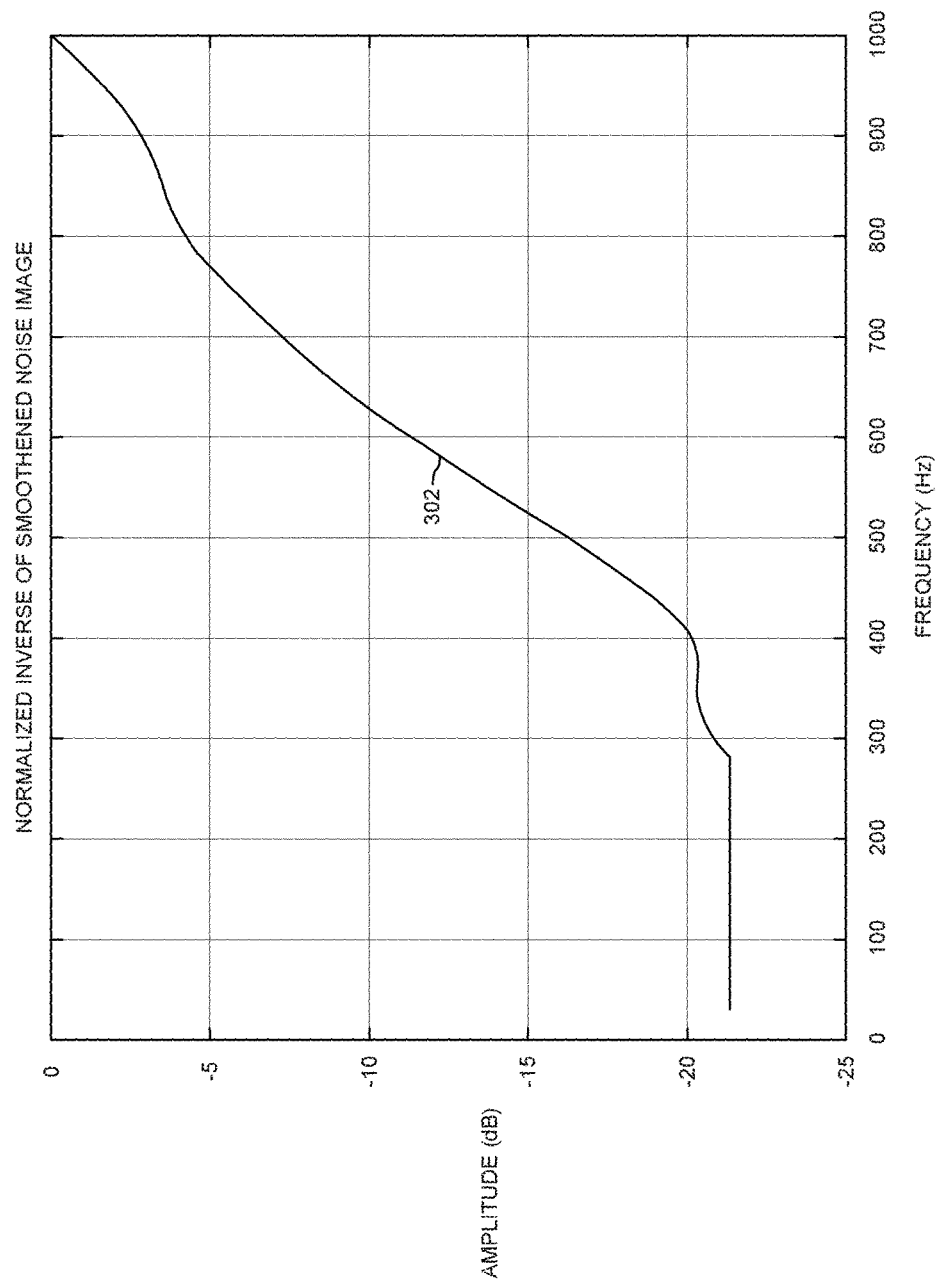
FIG. 3 depicts an example inverted and normalized smoothened noise image 302 in accordance with embodiments of the invention.

FIG. 3 depicts an example inverted and normalized smoothened noise image 302 in accordance with embodiments of the invention.

If this smoothened normalized inverse of the noise image was used as the $G_{min}$ curve for an input signal of pure noise, the output would closely resemble white noise. In automotive environments, however, we expect some amount of higher noise in the low frequencies, with this amount rolling off to a lower value in the higher frequencies. Therefore, in order to maintain this natural roll off, but remove excessive noise in the low frequency region, we allow the noise to follow a noise curve of a particular type. This could be, for example, pink noise, brown noise, or any other arbitrary noise type. The preferred noise type depends on the specific application, but the current embodiment uses a brown noise curve (power spectrum is proportional to $1/f^2$).

Any additional noise will be suppressed by allowing $G_{min}$ to go lower. To achieve this, we subtract our normalized inverse of the noise image from the normalized inverse of (brown) noise spectrum in the dB (log) domain, which is equivalent to division in the linear domain. First, the brown noise frequency spectrum is computed as follows:

$$BrownNoise[i] = \sqrt{\frac{1}{f(i)^2}}, i = 0, 1, \ldots, N-1$$

where f(i) is the frequency (in Hz) that corresponds to the starting point of the frequency channel i. The inverse is then computed and the result is normalized:

$$BrownNoise_{inv}[i] = \frac{1}{BrownNoise[i]}, i = 0, 1, \ldots, N-1$$

$$BrownNoise_{inv,norm}[i] = \frac{BrownNoise_{inv}[i]}{\max_{\forall i}(BrownNoise_{inv})}, i = 0, 1, \ldots, N-1$$

Figure 4:
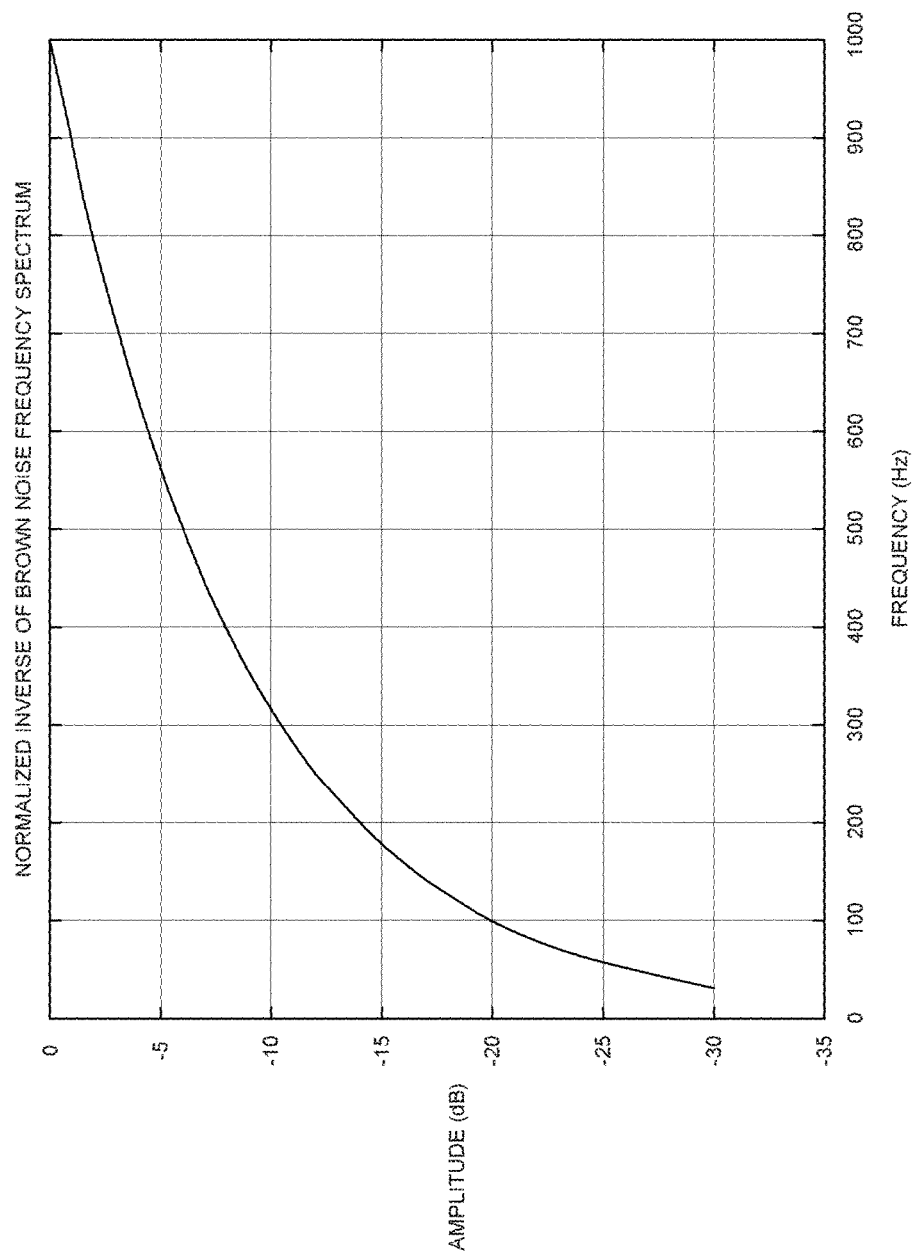
FIG. 4 depicts a normalized inverse of a brown noise spectrum with N corresponding to 1000 Hz in accordance with embodiments of the invention.

FIG. 4 depicts a normalized inverse of a brown noise spectrum with N corresponding to 1000 Hz in accordance with embodiments of the invention.

The $G_{adjust}$ curve is then computed:

$$G_{adjust}[i] = \min\left(\frac{\text{noise\_smooth}_{inv,norm}[i]}{BrownNoise_{inv,norm}[i]}, 1.0\right),$$

$i = 0, 1, \ldots, N-1$

Figure 5:
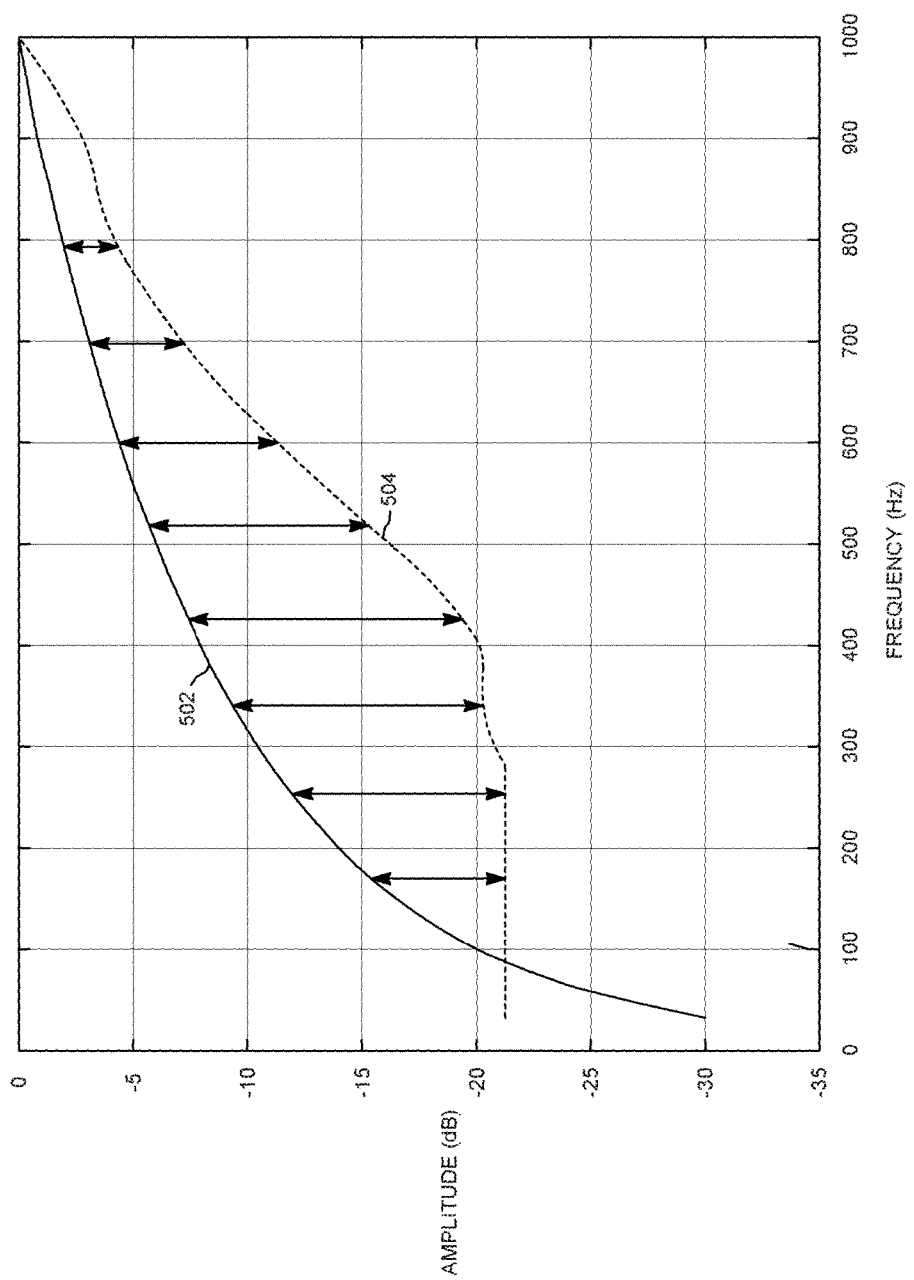
FIG. 5 depicts an example of a difference between the normalized inverse of brown noise frequency spectrum and the normalized inverse of the smoothened noise image.

Note that $G_{adjust}$ is limited to a maximum value of 1.0 in the linear domain (0 dB) to maintain the parameter-controlled $G_{min}$ as the maximum value in the $G_{min}$ curve. FIG. 5 depicts an example of a difference between the normalized inverse of brown noise frequency spectrum 502 and the normalized inverse of the smoothened noise image 504.

Figure 6:
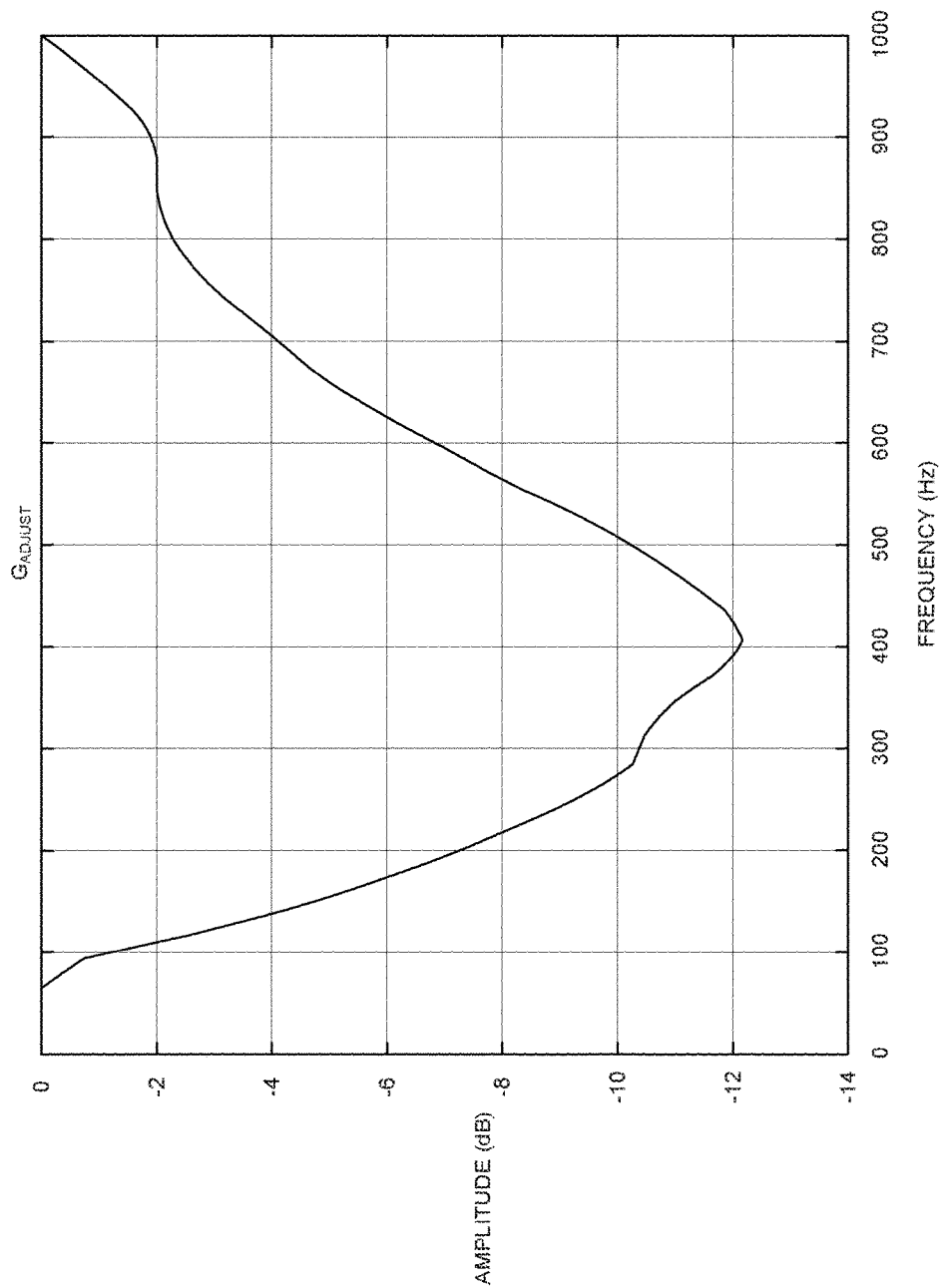
FIG. 6 depicts the $G_{adjust}$ curve that results by subtracting the normalized inverse of the smoothened noise image from the normalized inverse of brown noise frequency spectrum in accordance with embodiments of the invention.

FIG. 6 depicts the $G_{adjust}$ curve that results by subtracting the normalized inverse of the smoothened noise image from the normalized inverse of brown noise frequency spectrum in accordance with embodiments of the invention.

Figure 7:
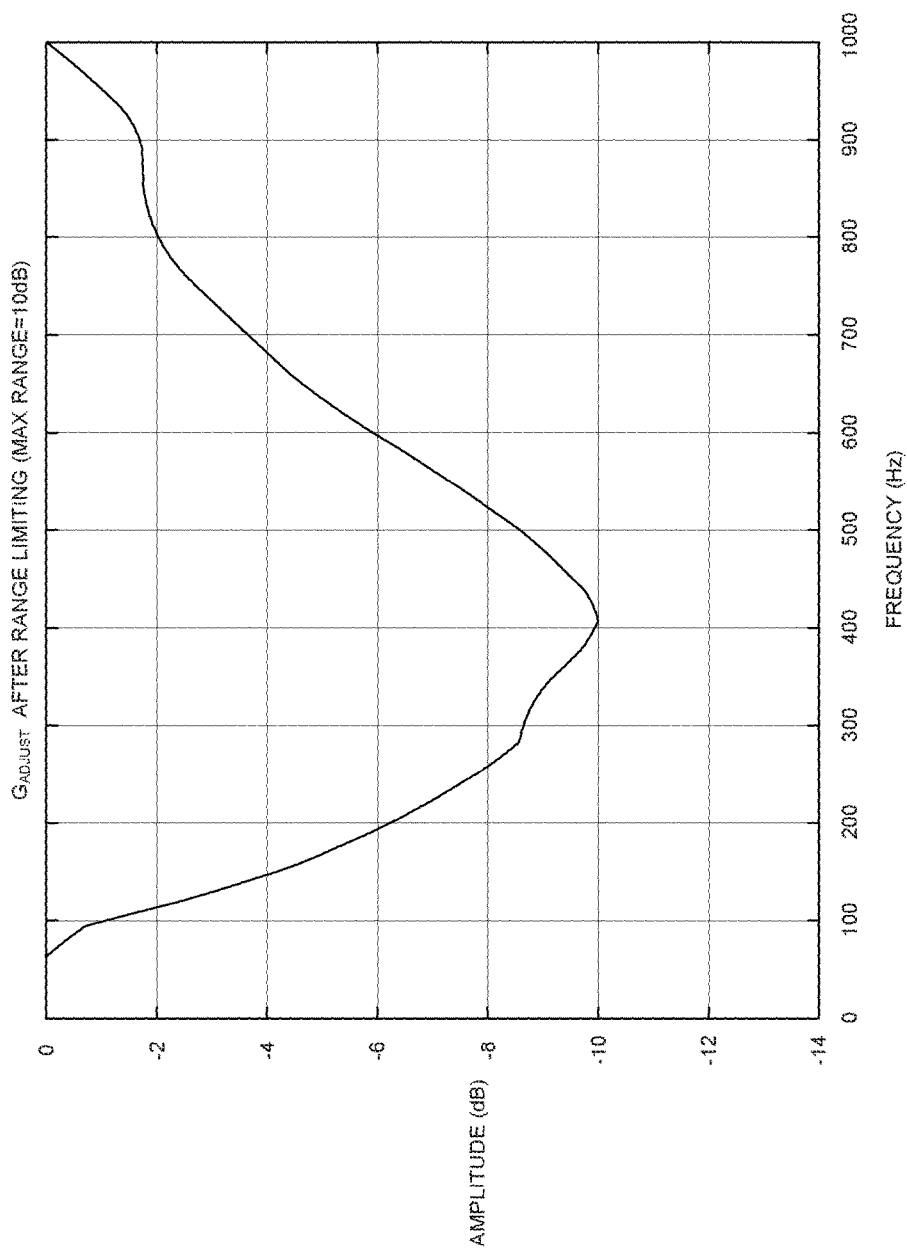
FIG. 7 shows an example parameter-controlled maximum range, maxRange, in accordance with embodiments of the invention.

In order to control the maximum level of noise suppression, if this $G_{adjust}$ curve exceeds a parameter-controlled range, it is limited to fit into that range:

$$G_{adjust}[i] = (a * G_{adjust}[i]) + b, i = 0, 1, \ldots, N-1$$

where $$a = \frac{1 - 10^{-maxRange/20}}{1 - \frac{\min(G_{adjust})}{\max(G_{adjust})}}$$

$$b = 1 - a$$

and maxRange is the parameter-controlled maximum range, specified in dB. An example value for the range is 10 dB. Other suitable values could also be used. FIG. 7 shows an example parameter-controlled maximum range, maxRange, in accordance with embodiments of the invention.

Figure 8:
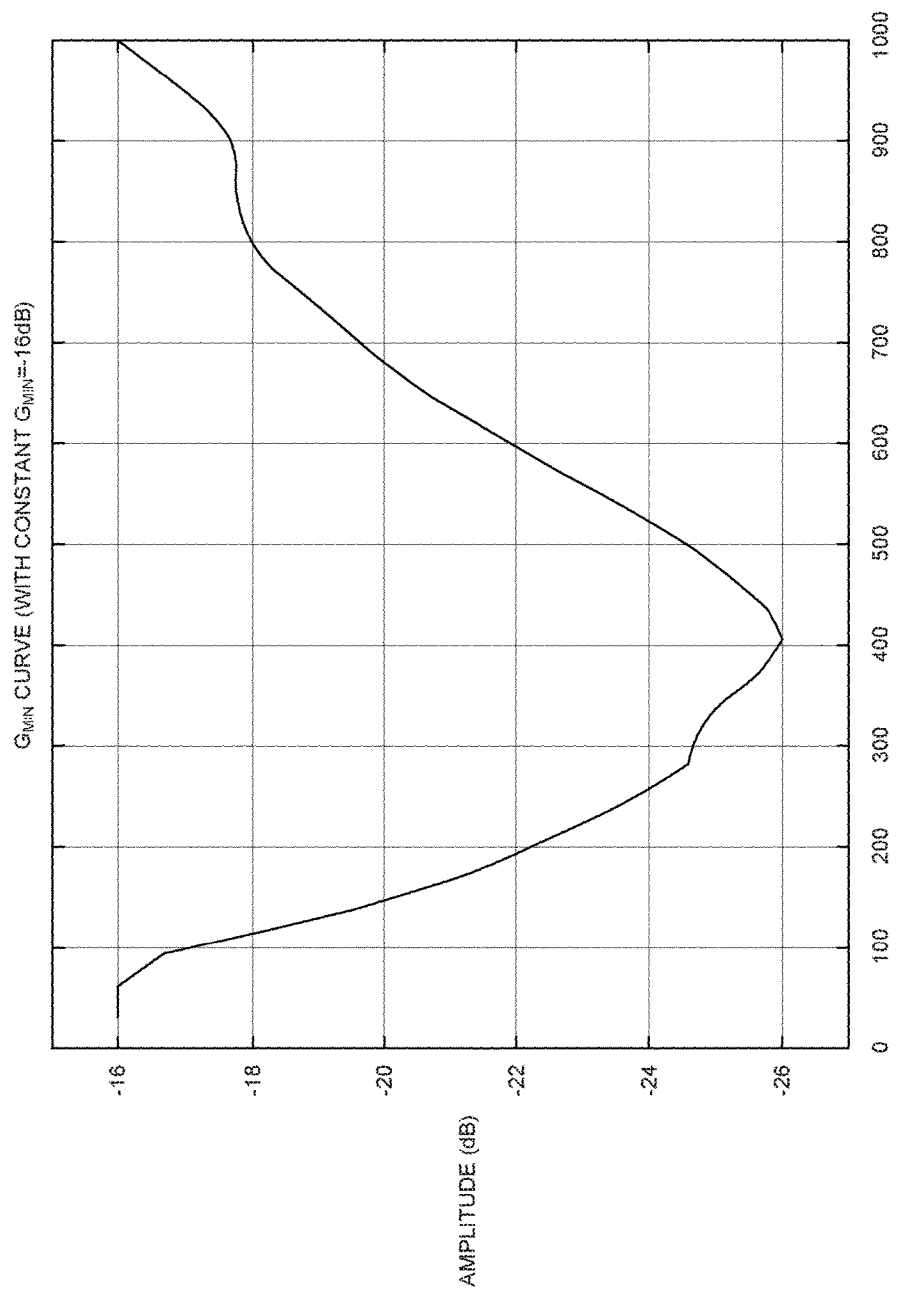
FIG. 8 shows an example $G_{min}$ curve in accordance with embodiments of the invention.

A $G_{min}$ curve is then computed by scaling the $G_{adjust}$ curve by the constant $G_{min}$ value. FIG. 8 shows an example $G_{min}$ curve in accordance with embodiments of the invention.

$$G_{min}\text{curve}[i] = G_{min} * G_{adjust}[i], i=0,1,\ldots,N-1$$

Figure 9:
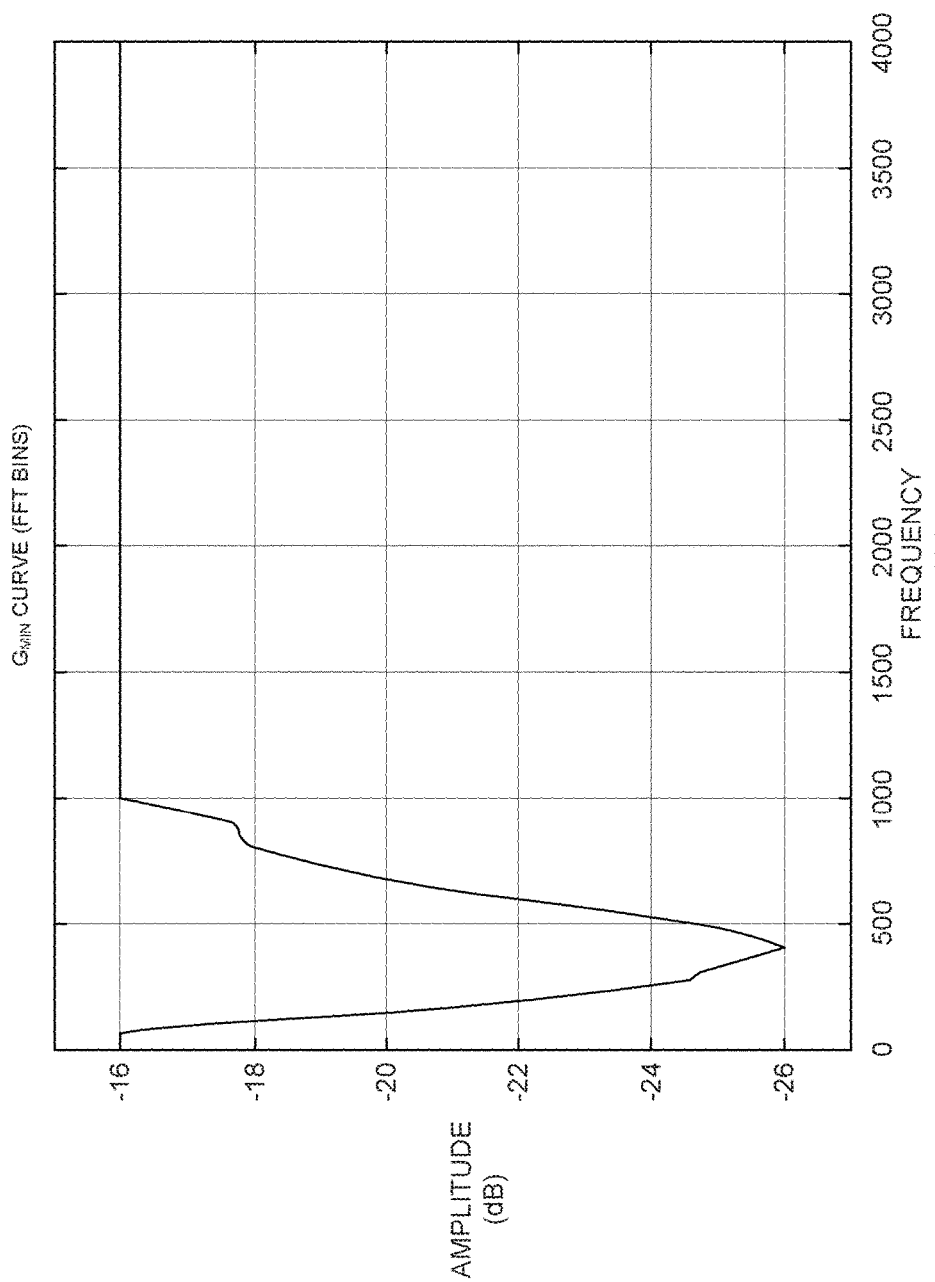
FIG. 9 shows an example $G_{min}$ curve from 0 through 4000 Hz in accordance with embodiments of the invention.

The curve is then interpolated from frequency channels to FFT bins. The remaining frequency channels (N and above) are set to the constant $G_{min}$ value. FIG. 9 shows an example $G_{min}$ curve from 0 through 4000 Hz in accordance with embodiments of the invention.

In this way, increased noise suppression occurs as is appropriate based on input noise characteristics. Since the noise suppression is based on the input noise characteristics, significantly less manual tuning of a hands-free audio system is required. As such, a consistent user experience of the audio system can be maintained for a similar vehicle cabin, even if various models of the vehicle are equipped with different engine types (e.g., gasoline vs. diesel engine).

In a second embodiment, the same framework described in the first embodiment may be extended to smoothen out the background noise that is output from the noise suppression.

In this embodiment, the adjustment curve is computed as the difference between the normalized inverse of the original noise image and the normalized inverse of smoothened noise image in the dB (log) domain, which is equivalent to division in the linear domain:

$$G_{adjust}[i] = \frac{noise\_orig_{inv,norm}[i]}{noise\_smooth_{inv,norm}[i]}, i = 0, 1, \ldots, N-1$$

Figure 10:
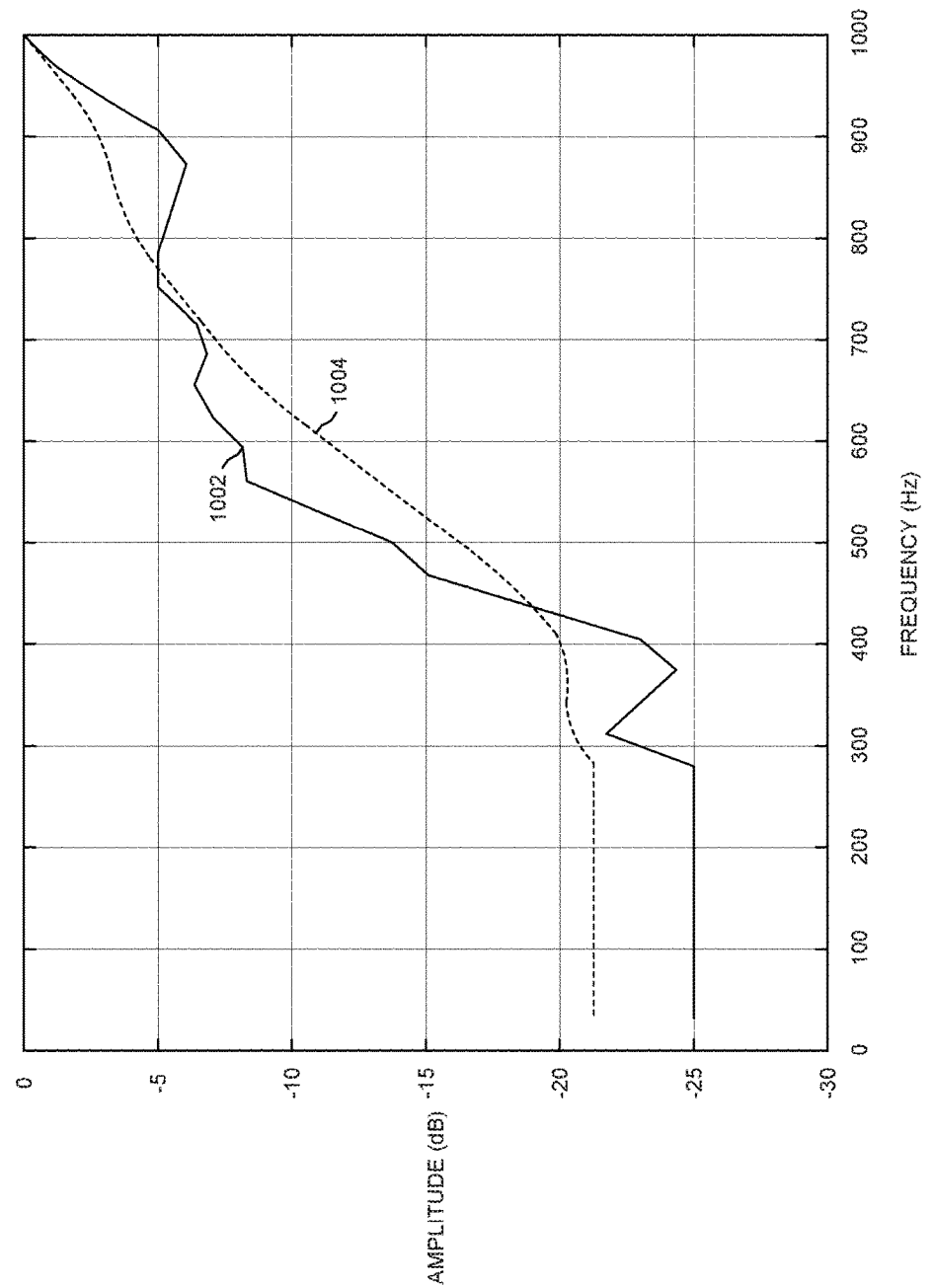
FIG. 10 depicts an example of the normalized inverse of the original noise image and the normalized inverse of smoothened noise image in accordance with embodiments of the invention.

Note that, in this case, $G_{adjust}$ is not limited, so the value can be greater than 1.0. FIG. 10 depicts an example of the normalized inverse of the original noise image 1002 and the normalized inverse of smoothened noise image 1004 in accordance with embodiments of the invention.

Figure 11:
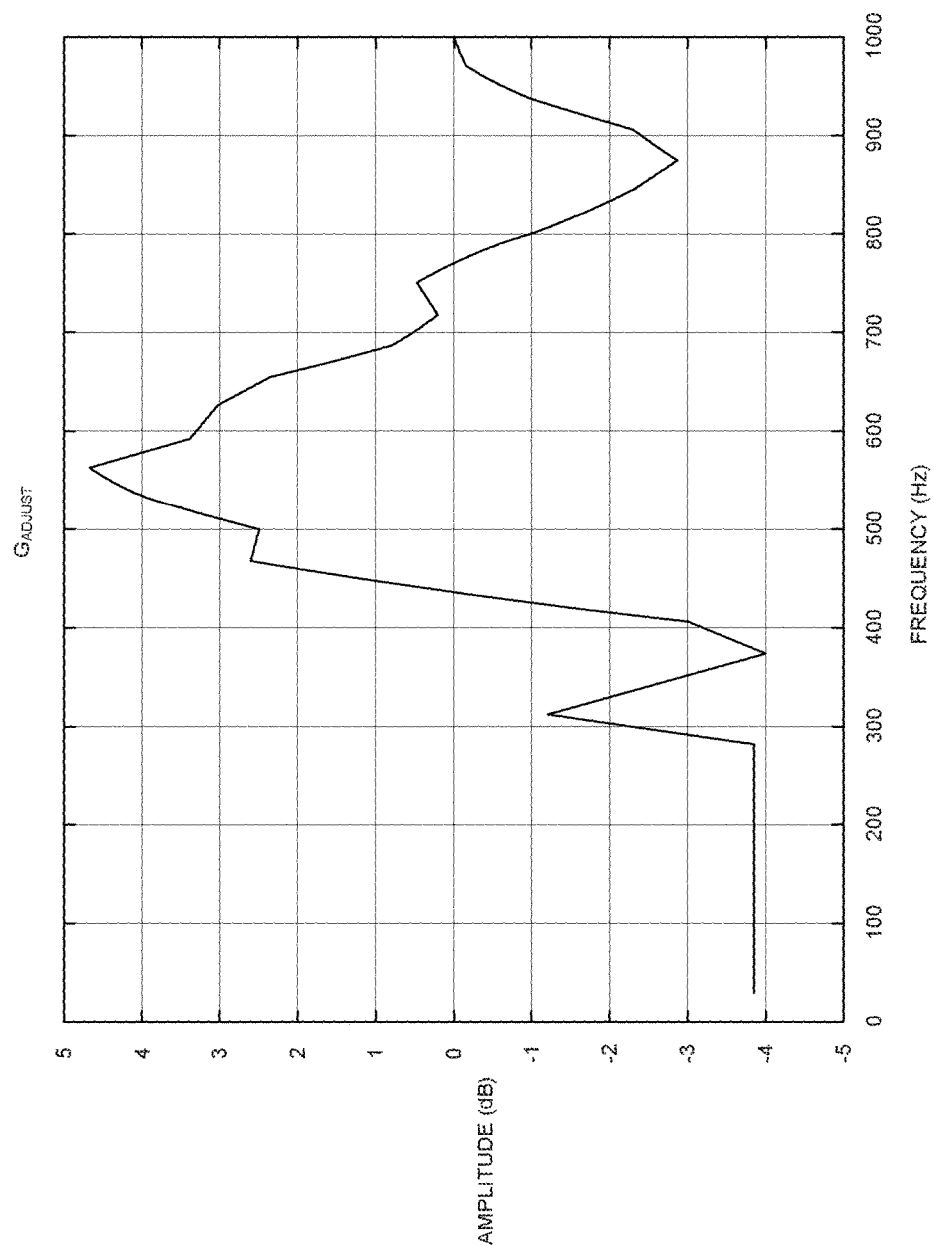
FIG. 11 depicts the $G_{adjust}$ curve calculated by subtracting the normalized inverse of smoothened noise image from the normalized inverse of the original noise image in accordance with embodiments of the invention.

FIG. 11 depicts the $G_{adjust}$ curve calculated by subtracting the normalized inverse of smoothened noise image 1004 from the normalized inverse of the original noise image 1002, in accordance with embodiments of the invention.

The remaining computations described above in connection with the first embodiment for limiting the range and computing the $G_{min}$ curve may also be performed in the second embodiment.

In a third embodiment, the two different $G_{adjust}$ curves described in the first embodiment and the second embodiment may be combined to achieve both goals in the output signal, namely, less low frequency noise and smoothened background noise.

Figure 12:
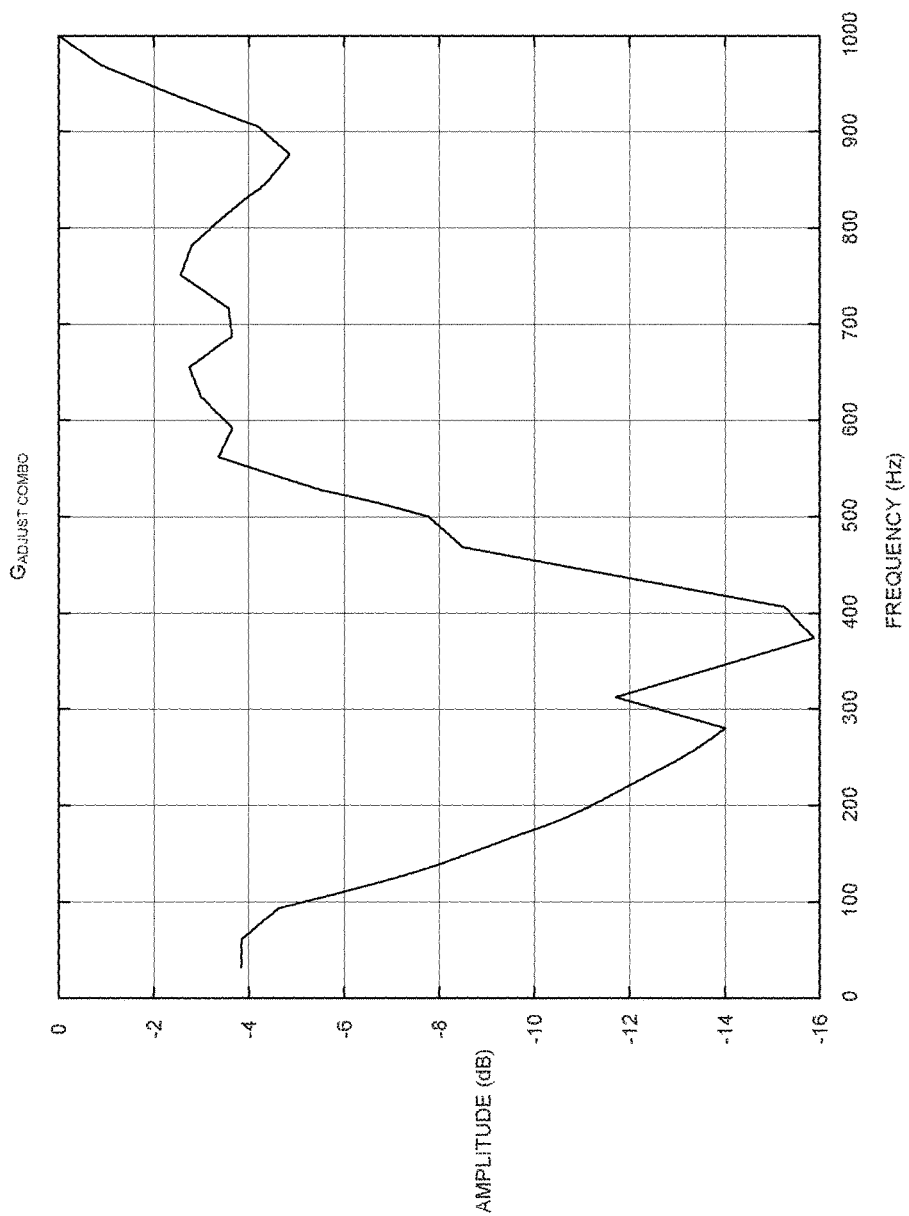
FIG. 12 depicts an example adjust, $G_{adjust,combo}$ in accordance with embodiments of the invention.

Specifically, the $G_{adjust}$ curves can be added in the dB (log) domain, which is equivalent to multiplication in the linear domain:

$$G_{adjust,combo}[i] = G_{adjust,1}[i] * G_{adjust,2}[i], i=0,1,\ldots,N-1$$

where $G_{adjust,1}$ is the $G_{adjust}$ computed in accordance with the first embodiment and $G_{adjust,2}$ is the $G_{adjust}$ computed in accordance with the second embodiment. FIG. 12 depicts an example $G_{adjust,combo}$ in accordance with embodiments of the invention.

The remaining computations described above in connection with the first embodiment for limiting the range and computing the $G_{min}$ curve may also be performed in the third embodiment.

In accordance with embodiments of the invention excess low-frequency noise may be removed while maintaining speech quality and/or smoothening out background noise.

The invention claimed is:

1. A method comprising:
   smoothening an original noise image over a first frequency range to form a smoothened noise image, wherein the first frequency range includes a first plurality of frequency channels over which the original noise image is smoothened;
   inverting the smoothened noise image to produce an inverted smoothened noise image;
   normalizing the inverted smoothened noise image to produce an inverted and normalized smoothened noise image;
   allowing the noise to follow a noise curve of a particular type;
   calculating a gain-adjustment curve ($G_{adjust}$ curve) by subtracting the normalized inverse of the smoothened noise image from a normalized inverse of the noise curve in the dB (log) domain;
   to control a maximum level of noise suppression, if the $G_{adjust}$ curve exceeds a parameter-controlled range, limiting the $G_{adjust}$ curve to fit into parameter-controlled range;
   computing a minimum gain curve by scaling the gain-adjustment curve by a constant minimum gain value;
   interpolating the minimum gain curve from the first plurality of frequency channels to a first plurality of Fast Fourier Transform (FFT) bins over the first frequency range; and
   setting a second plurality of FFT bins for a plurality of frequency channels outside the first frequency range to the constant minimum gain value.

2. The method of claim 1, wherein smoothening the original noise image over the first frequency range comprises low-pass filtering the original noise image.

3. The method of claim 1, wherein the first frequency range is approximately 0 Hz to approximately 1000 Hz.

4. The method of claim 1, wherein the particular type of noise curve is a brown noise curve.

5. The method of claim 4, further comprising computing the brown noise curve as follows:

$$BrownNoise[i] = \sqrt{\frac{1}{f(i)^2}}, i = 0, 1, \ldots, N-1$$

where f(i) is a frequency (in Hz) that corresponds to a starting point of a frequency channel I,
computing an inverse of the brown noise curve as follows:

$$BrownNoise_{inv}[i] = \frac{1}{BrownNoise[i]}, i = 0, 1, \ldots, N-1$$

normalizing the inverse of the brown noise curve as follows:

$$BrownNoise_{inv,norm}[i] = \frac{BrownNoise_{inv}[i]}{\max_{\forall i}(BrownNoise_{inv})}, i = 0, 1, \ldots, N-1$$

to produce a normalized inverse of the brown noise curve.

6. The method of claim 1, wherein calculating the gain-adjustment curve by subtracting the normalized inverse of the smoothened noise image from a normalized inverse of the noise curve in the dB (log) domain further comprises computing:

$$G_{adjust}[i] = \min\left(\frac{noise\_smooth_{inv,norm}[i]}{BrownNoise_{inv,norm}[i]}, 1.0\right),$$
$$i = 0, 1, \ldots, N-1.$$

7. The method of claim 1, wherein the minimum gain curve is computed as follows:

$$G_{min}\text{curve}[i] = G_{min} * G_{adjust}[i], i = 0, 1, \ldots, N-1$$

8. A method comprising:
smoothening an original noise image over a first frequency range to form a smoothened noise image, wherein the first frequency range includes a first plurality of frequency channels over which the original noise image is smoothened;
inverting the smoothened noise image to produce an inverted smoothened noise image;
normalizing the inverted smoothened noise image to produce an inverted and normalized smoothened noise image;
inverting the original noise image to produce an inverted original noise image;
normalizing the inverted noise image to produce an inverted and normalized original noise image;
calculating a gain-adjustment curve ($G_{adjust}$ curve) as a difference between the normalized inverse of the original noise image and the normalized inverse of the smoothened noise image in the dB (log) domain
computing a minimum gain curve by scaling the gain-adjustment curve by a constant minimum gain value;
interpolating the minimum gain curve from the first plurality of frequency channels to a first plurality of Fast Fourier Transform (FFT) bins over the first frequency range; and
setting a second plurality of FFT bins for a plurality of frequency channels outside the first frequency range to the constant minimum gain value.

9. The method of claim 8, wherein smoothening the original noise image over the first frequency range comprises low-pass filtering the original noise image.

10. The method of claim 8, wherein the first frequency range is approximately 0 Hz to approximately 1000 Hz.

11. The method of claim 8, wherein calculating the gain-adjustment curve further comprises computing:

$$G_{adjust}[i] = \frac{noise\_orig_{inv,norm}[i]}{noise\_smooth_{inv,norm}[i]}, i = 0, 1, \ldots, N-1.$$

12. The method of claim 8, wherein the minimum gain curve is computed as follows:

$$G_{min}\text{curve}[i] = G_{min} * G_{adjust}[i], i = 0, 1, \ldots, N-1$$

13. A method comprising:
smoothening an original noise image over a first frequency range to form a smoothened noise image, wherein the first frequency range includes a first plurality of frequency channels over which the original noise image is smoothened;
inverting the smoothened noise image to produce an inverted smoothened noise image;
normalizing the inverted smoothened noise image to produce an inverted and normalized smoothened noise image;
allowing the noise to follow a noise curve of a particular type;
calculating a first gain-adjustment curve ($G_{adjust,1}$ curve) by subtracting the normalized inverse of the smoothened noise image from a normalized inverse of the noise curve in the dB (log) domain;
to control a maximum level of noise suppression, if the $G_{adjust}$ curve exceeds a parameter-controlled range, limiting the $G_{adjust}$ curve to fit into parameter-controlled range;
inverting the original noise image to produce an inverted original noise image;
normalizing the inverted noise image to produce an inverted and normalized original noise image;
calculating a second gain-adjustment curve ($G_{adjust,2}$ curve) as a difference between the normalized inverse of the original noise image and the normalized inverse of the smoothened noise image in the dB (log) domain;
adding the first gain-adjustment curve and the second gain-adjustment curve in the dB (log) domain to produce a combined gain-adjustment curve;
computing a minimum gain curve by scaling the combined gain-adjustment curve by a constant minimum gain value;
interpolating the minimum gain curve from the first plurality of frequency channels to a first plurality of Fast Fourier Transform (FFT) bins over the first frequency range; and
setting a second plurality of FFT bins for a plurality of frequency channels outside the first frequency range to the constant minimum gain value.

14. The method of claim 13, wherein smoothening the original noise image over the first frequency range comprises low-pass filtering the original noise image.

15. The method of claim 13, wherein the particular type of noise curve is a brown noise curve.

16. The method of claim 15, further comprising computing the brown noise curve as follows:

$$BrownNoise[i] = \sqrt{\frac{1}{f(i)^2}}, i = 0, 1, \ldots, N-1$$

where f(i) is a frequency (in Hz) that corresponds to a starting point of a frequency channel I;

computing an inverse of the brown noise curve as follows:

$$BrownNoise_{inv}[i] = \frac{1}{BrownNoise[i]}, i = 0, 1, \ldots, N-1$$

normalizing the inverse of the brown noise curve as follows:

$$BrownNoise_{inv,norm}[i] = \frac{BrownNoise_{inv}[i]}{\max_{\forall i}(BrownNoise_{inv})}, i = 0, 1, \ldots, N-1$$

to produce a normalized inverse of the brown noise curve.

17. The method of claim 13, wherein calculating the first gain-adjustment curve by subtracting the normalized inverse of the smoothened noise image from a normalized inverse of the noise curve in the dB (log) domain further comprises computing:

$$G_{adjust,1}[i] = \min\left(\frac{\text{noise\_smooth}_{inv,norm}[i]}{BrownNoise_{inv,norm}[i]}, 1.0\right),$$
$$i = 0, 1, \ldots, N-1.$$

18. The method of claim 13, wherein calculating the second gain-adjustment curve further comprises computing:

$$G_{adjust,2}[i] = \frac{\text{noise\_orig}_{inv,norm}[i]}{\text{noise\_smooth}_{inv,norm}[i]}, \quad i = 0, 1, \ldots, N-1.$$

19. The method of claim 13, wherein adding the first gain-adjustment curve and the second gain-adjustment curve in the dB (log) domain comprises calculating:

$$G_{adjust,combo}[i] = G_{adjust,1}[i] * G_{adjust,2}[i], i = 0, 1, \ldots, N-1$$

20. The method of claim 13, wherein the minimum gain curve is computed as follows:

$$G_{min}\text{curve}[i] = G_{min} * G_{adjust,combo}[i], i = 0, 1, \ldots, N-1.$$

* * * * *